(12) United States Patent
Wang et al.

(10) Patent No.: US 8,765,188 B2
(45) Date of Patent: Jul. 1, 2014

(54) COMPOSITION FOR TREATING AND/OR PREVENTING OSTEOPOROSIS

(75) Inventors: Ching-Chiung Wang, Taipei (TW); Sung-Hui Tseng, Taipei (TW); Chun-Hsien Sung, Taipei (TW)

(73) Assignee: Taipei Medical University, Taipei (TW)

( * ) Notice: Subject to any disclaimer, the term of this patent is extended or adjusted under 35 U.S.C. 154(b) by 186 days.

(21) Appl. No.: 13/241,722

(22) Filed: Sep. 23, 2011

(65) Prior Publication Data

US 2013/0078311 A1    Mar. 28, 2013

(51) Int. Cl.
*A61K 35/14*        (2006.01)
*A61K 35/32*        (2006.01)
*A61K 33/26*        (2006.01)

(52) U.S. Cl.
CPC .................. *A61K 35/14* (2013.01); *A61K 35/32* (2013.01); *A61K 33/26* (2013.01)
USPC ........................................................ 424/529

(58) Field of Classification Search
CPC ....... A61K 35/12; A61K 35/14; A61K 35/32; A61K 33/26
USPC ........................................................ 424/520
See application file for complete search history.

(56) References Cited

U.S. PATENT DOCUMENTS 7,387,781  B2    6/2008   Kadota et al.
2003/0044470  A1    3/2003   Wani et al.

FOREIGN PATENT DOCUMENTS

CN         1249337      *   4/2000

OTHER PUBLICATIONS

English Translations of: 1) Office Action of TW Application No. 100135168 dated Sep. 23, 2013; 2) "Velent antler for improving osteoporosis"; and 3) "Effect of Velent Antler Blood".

* cited by examiner

*Primary Examiner* — Ruth Davis
(74) *Attorney, Agent, or Firm* — WPAT, P.C.; Anthony King

(57) ABSTRACT

The invention relates to a composition comprising deer velvet antler blood (DVAB) in combination with velvet antler for use in the treatment and/or prevention of osteoporosis and a method for treating and/or preventing osteoporosis, comprising administering a therapeutically effective amount of a composition comprising DVAB and velvet antler to a subject at risk of developing or afflicted with osteoporosis. The composition of the invention, when administered to a subject with osteoporosis, increases anti-osteoporotic activity, decreases the biomarker of osteoporosis and recovers the biomechanical strength and structure of bone, suggesting that the said composition could significantly prevent and even treat osteoporosis.

13 Claims, 4 Drawing Sheets

COMPOSITION FOR TREATING AND/OR PREVENTING OSTEOPOROSIS

FIELD OF THE INVENTION

The present invention relates to a composition for the treatment and/or prevention of osteoporosis. Particularly, the composition of the invention comprises deer velvet antler blood (DVAB) in combination with velvet antler for use in the treatment and/or prevention of osteoporosis.

BACKGROUND OF THE INVENTION

Bone is a supporting material for the body's framework and conserves the necessary bone mass and structure. Bone also functions as a reservoir of calcium ($Ca^{2+}$) or the like, and plays an important role in maintaining calcium level in the blood. Bone is in a dynamic steady state of bone remodeling, which maintains a delicate balance by continuously performing both bone resorption and bone formation. Bone remodeling is a complex process involving bone formation by osteoblasts and bone resorption and degradation by osteoclasts, thereby maintaining a physiological and metabolic balance. However, the balance between bone resorption and bone formation is disrupted by various factors and diseases, leading to osteoporosis.

Osteoporosis is a bone disease which results from a disturbance in the balance between bone resorption and bone formation, caused by having a higher degree of bone resorption relative to bone formation. This disease frequently occurs in middle-aged or elderly women. Osteoporosis reduces calcification of bone tissues, and decreases the level of compact substances in the bone, which broadens the marrow cavity, and causes reduction in bone density or bone mass, resulting in decreased bone strength. Consequently, as osteoporosis progresses, bone becomes brittle, and fracture may easily occur even with a small impact. Bone fracture is associated with an increased mortality rate of patients with osteoporosis, and also causes serious problems such as negative impact on patients' quality of life. Thus, various strategies have been established to produce drugs capable of increasing bone density and decreasing of the risk of bone fracture.

Bisphosphonate (alendronate, etidronate), hormones (raloxifen), vitamin D, calcitonin, calcium agents, or the like have been used as anti-osteoporotic agents, and Forteo™, a form of parathyroid hormone responsible for bone formation, is currently used to treat advanced osteoporosis. However, they are known to have adverse effects. Specifically, hormone agents must be administered throughout the patient's life, and in the case of long-term administration, side effects may be induced such as breast cancer, uterus cancer, gallstones and thrombosis. Vitamin D agents are expensive and show little efficacy, and calcitonin agents are also very expensive and difficult to administer. Calcium agents have few side effects, but their effectiveness is restricted to prevention of osteoporosis, not treatment. Forteo™, a commercially available parathyroid hormone, has an advantage in that it stimulates bone formation, whereas other known drugs are restricted to prevention of bone resorption. However, Forteo™ should be given as a daily injection for a long period of time, and may increase the risk of osteosarcoma. Its application is also restricted due to its relatively high price.

Bisphosphonate agents show low absorptivity and may induce esophagitis, and thus should be taken with a sufficient amount of water before meals. In addition, patients should wait at least 30 minutes before ingesting other beverage or food, and avoid lying down for a prescribed amount of time following administration. Such agents are also reported to increase risk of hypocalcemia. Recent studies have suggested problems such as reduction in bone turnover rate due to excessive inhibition of bone resorption, inhibition of bone formation, gastrointestinal disorders and osteonecrosis of the jaw. Furthermore, it has recently been reported that long term administration increases the risk of bone fractures.

As described above, the current therapeutic agents for osteoporosis have drawbacks, so there is a need for development of osteoporosis drugs and therapies which have reduced disadvantages or side effects. Natural products from plants and organisms have frequently been used as sources for development of effective drugs. There is increased interest, for example, in analysis of natural products from marine organisms. US Patent Publication No. 2003066083 provides a novel extract (mussel hydrolysate) prepared from the Indian green mussel (Perna viridis), which can inhibit osteoclast differentiation in murine haemopoietic precursors of monocyte/macrophage cell lineage. U.S. Pat. No. 7,387,781 provides a composition for treating osteoporosis and osteoclast formation, comprising C. Sinensis mycelium as the effective ingredient.

Deer velvet antler and deer velvet antler blood (DVAB) are famous traditional Chinese medicines commonly used as tonics against stress and fatigue. However, no prior art references teach or suggest that deer velvet antler and DVAB have benefits in regard to osteoporosis.

SUMMARY OF THE INVENTION

The invention provides a composition for treating and/or preventing osteoporosis in a subject, comprising DVAB and velvet antler.

The invention also provides a method for treating and/or preventing osteoporosis, comprising administering a therapeutically effective amount of a composition comprising DVAB and velvet antler to a subject at risk of developing or afflicted with osteoporosis.

DETAILED DESCRIPTION OF THE INVENTION

Figure 1:
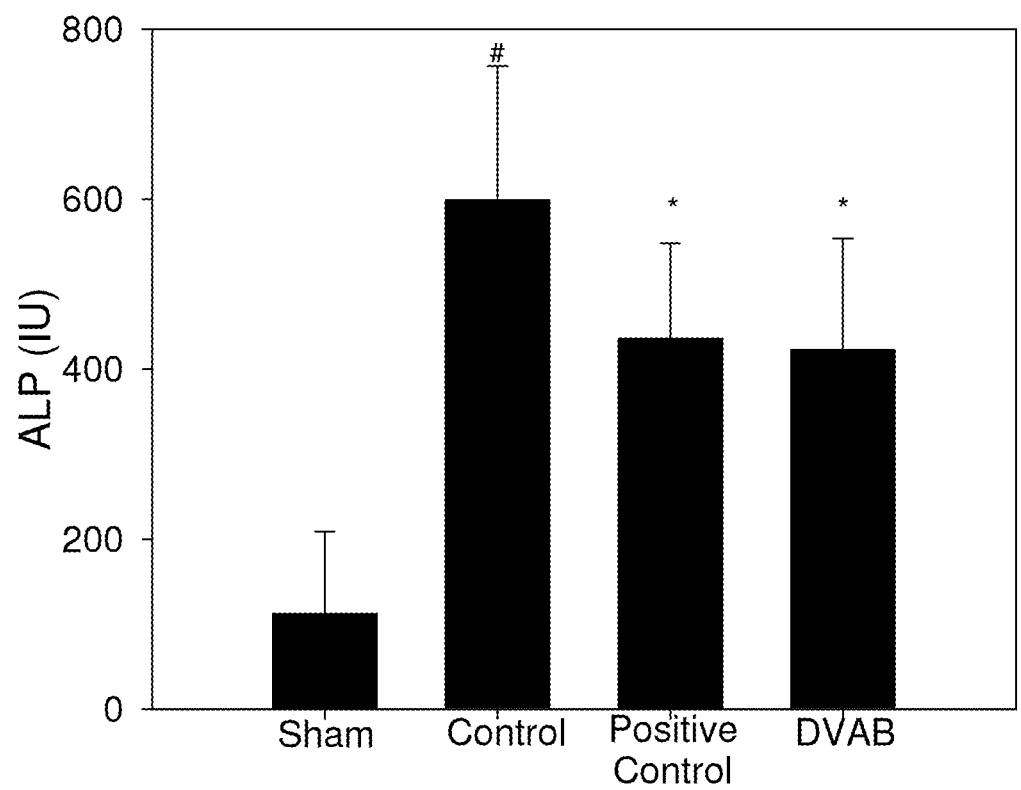
FIG. 1 shows the ALP values in rats. #: $p<0.05$ vs sham group; *: $p<0.05$ vs control group.

The invention surprisingly found that deer velvet antler blood composition can significantly treat and/or prevent osteoporosis.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The terms "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 40%, 30%, 20% or 10% to a reference quantity, level, value, dimension, size, or amount.

Throughout this specification, unless the context requires otherwise, the words "comprise," "comprises" and "comprising" will be understood to imply the inclusion of a stated step or element or group of steps or elements but not the exclusion of any other step or element or group of steps or elements.

By "effective amount," in the context of treating or preventing a condition, is meant the administration of that amount of active ingredient to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

By "acceptable carrier" is meant a solid or liquid filter, diluent or encapsulating substance that may be safely used in topical, local or systemic administration.

The term "pharmaceutically acceptable salt" as used herein refers to a salt which is toxicologically safe for human and animal administration. This salt may be selected from a group including hydrochlorides, hydrobromides, hydroiodides, sulphates, bisulphates, nitrates, citrates, tartrates, bitartrates, phosphates, malates, maleates, napsylates, fumarates, succinates, acetates, terephthalates, pamoates and pectinates.

The terms "subject" or "individual" or "patient," used interchangeably herein, refer to any subject, particularly a vertebrate subject, and even more particularly a mammalian subject, for whom therapy or prophylaxis is desired. Vertebrate animals that fall within the scope of the invention include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). An example of a subject is a human in need of treatment or prophylaxis for osteoporosis condition. However, it will be understood that the aforementioned terms do not imply that symptoms are present.

The present invention arises from the discovery that deer velvet antler blood (DVAB) in combination with velvet antler is effective in treating and/or preventing osteoporosis. Additionally, a composition comprising DVAB and velvet antler, when administered to a subject with osteoporosis, increases anti-osteoporotic activity, decreases the biomarker of osteoporosis and recovers the biomechanical strength and structure of bone, suggesting that the said composition could significantly prevent and even treat osteoporosis.

Accordingly, in one aspect, the present invention provides a composition for treating and/or preventing osteoporosis in a subject, comprising DVAB and velvet antler. In another aspect, the present invention provides methods for treating and/or preventing osteoporosis, comprising administering a therapeutically effective amount of a composition comprising DVAB and velvet antler to a subject at risk of developing or afflicted with osteoporosis.

According to the invention, the composition can be used as a medicament or a food (such as a dietary supplement).

In one embodiment, the compositions containing DVAB and velvet antler will generally contain about 5% (w/w) to about 50% (w/w) of DVAB and about 95% (w/w) to about 50% (w/w) of velvet antler. Preferably, the amount of DVAB ranges from about 5% (w/w) to about 45% (w/w), about 5% (w/w) to about 40% (w/w), about 5% (w/w) to about 35% (w/w), about 5% (w/w) to about 30% (w/w), about 5% (w/w) to about 25% (w/w), about 5% (w/w) to about 20% (w/w), about 10% (w/w) to about 20% (w/w), about 10% (w/w) to about 25% (w/w), about 10% (w/w) to about 30% (w/w), about 10% (w/w) to about 35% (w/w), about 10% (w/w) to about 30% (w/w) or about 10% (w/w) to about 25% (w/w); more preferably, about 10% (w/w) to about 35% (w/w), about 10% (w/w) to about 30% (w/w) or about 10% (w/w) to about 25% (w/w). Preferably, the amount of velvet antler ranges from about 95% (w/w) to about 55% (w/w), about 95% (w/w) to about 60% (w/w), about 95% (w/w) to about 65% (w/w), about 95% (w/w) to about 70% (w/w) or about 95% (w/w) to about 75% (w/w), about 95% (w/w) to about 80% (w/w), about 90% (w/w) to about 55% (w/w), about 90% (w/w) to about 55% (w/w), about 90% (w/w) to about 60% (w/w), about 90% (w/w) to about 65% (w/w), about 90% (w/w) to about 70% (w/w), about 90% (w/w) to about 75% (w/w) or about 90% (w/w) to about 80% (w/w); more preferably, about 90% (w/w) to about 65% (w/w), about 90% (w/w) to about 70% (w/w), about 90% (w/w) to about 75% (w/w) or about 90% (w/w) to about 80% (w/w).

According to the invention, the composition of the invention contains higher amount of iron. For example, the amount of iron in the composition ranging from about 200 ppm to about 500 ppm; preferably, about 250 ppm to about 500 ppm, about 300 ppm to about 500 ppm, about 350 ppm to about 500 ppm, about 400 ppm to about 500 ppm or about 250 ppm to about 450 ppm; more preferably, about 300 ppm to about 500 ppm, about 350 ppm to about 500 ppm, about 400 ppm to about 500 ppm or about 400 ppm to about 450 ppm.

According to the invention, a daily dose of the composition of the invention may be from about 10 mg/kg body weight (BW) to about 300 mg/kg of BW per day, from about 100 mg to 200 mg/kg BW or about 200 mg/kg BW. The dosage of the composition can depend on a variety of factors, such as mode of administration, the species of the affected subject, age and/or individual condition.

The term "deer velvet" is the name given to male deer and elk antlers during growth, before they harden into weapons for territorial defense and fighting. Deer velvet antler is the antler of male deer during the phase of rapid growth, so called because of the velvet-like covering of skin. Deer velvet is the only known mammalian organ that is generated in this way. Deer antlers grow at incredible speed and, after several weeks, as the antlers reach their final size, the cartilage within them gradually converts into bone. In the final process, the antler's blood supply and nerves are lost. Deer antler is harvested from deer raised on ranches. At the ideal time of the year, the antlers are removed and specially processed to make the natural components bioavailable to the human body. According to the invention, deer antler or an extract thereof can be used in the invention. In one embodiment, deer velvet can be prepared as an extract. Preferably, the deer velvet is extracted by ethanol. According to the invention, DVAB is collected by cutting deer velvet.

Compositions that can be used in the present invention include compositions wherein the active components are contained in an effective amount to achieve their intended purpose. The dose of active components administered to a patient should be sufficient to achieve a beneficial response in the patient over time such as a prevention or reduction in at least one symptom associated with osteoporosis. The quantity of the active components to be administered may depend on the subject to be treated inclusive of the age, sex, weight and general health condition thereof. In this regard, precise amounts of the active components for administration will depend on the judgment of the practitioner. In determining the effective amount of the active compound(s) to be administered in the prophylaxis of the osteoporosis, the physician may evaluate numbness, weakness, pain, and loss of reflexes.

According to the invention, deer velvet and DVAB are mixed to obtain the composition of the invention. In one embodiment, fresh deer velvet can be sliced, dried and then ground into powder. Deer velvet antler blood is collected from deer and then mixed with the deer velvet powder to produce the composition of the invention.

The subject to be administered can be an individual who has been diagnosed with osteoporosis, who is suspected of having osteoporosis, who is known to be susceptible and who is considered likely to develop osteoporosis, or who is considered likely to develop a recurrence of a previously treated osteoporosis.

The active components may be formulated and administered systemically, topically or locally. Techniques for formulation and administration may be found in "Remington's Pharmaceutical Sciences," Mack Publishing Co., Easton, Pa., latest edition. Suitable routes may include, for example, oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. For injection, the therapeutic agents of the invention may be formulated in aqueous solutions, suitably in physiologically compatible buffers such as Hanks' solution, Rinter's solution, or physiological saline buffer. For transmucosal administration, penetrants appropriate to the barrier to be permeated are used in the formulation. Such penetrants are generally known in the art.

The compositions of this invention may be further formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

Alternatively, the active components of the present invention can be formulated readily using pharmaceutically acceptable carriers well known in the art into dosages suitable for oral administration, which is also preferred for the practice of the present invention. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatin, talc, calcium sulphate, vegetable oils, synthetic oils, polyols, alginic acid, phosphate buffered solutions, emulsifiers, isotonic saline, and pyrogen-free water.

Compositions for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active compounds to allow for the preparation of highly concentrated solutions.

Compositions for oral use can be obtained by combining the active components with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose-, sodium caroxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more therapeutic agents as described above with the carrier which constitutes one or more necessary ingredients. In general, the compositions of the present invention may be manufactured in a manner that is itself known, e.g., by means of conventional mixing, dissolving, granulating, dragee-making, levigating, emulsifying, encapsulating, entrapping or lyophilising processes.

Dragee cores can be provided with coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Dosage forms of the active components of the invention may also include injecting or implanting controlled releasing devices designed specifically for this purpose or other forms of implants modified to act additionally in this fashion. Controlled release of active components of the invention may be achieved by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be achieved by using other polymer matrices, liposomes and/or microspheres.

The active components of the invention may be administered over a period of hours, days, weeks, or months, depending on several factors, including the severity of the osteoporosis being treated, whether a recurrence of the condition is considered likely, etc. The administration may be constant, e.g., constant infusion over a period of hours, days, weeks, months, etc. Alternatively, the administration may be intermittent, e.g., active compounds may be administered once a day over a period of days, once an hour over a period of hours, or any other such schedule as deemed suitable.

The compositions of the present invention may also be administered to the respiratory tract as a nasal or pulmonary inhalation aerosol or solution for a nebuliser, or as a microfine powder for insufflation, alone or in combination with an inert carrier such as lactose, or with other pharmaceutically acceptable excipients.

In order that the invention may be readily understood and put into practical effect, particular embodiments will now be described by way of the following non-limiting examples.

EXAMPLES

Example 1

In vitro Assay for Enhancing Survival Rate of MC3T3-E1 Cells by the Composition of the Invention DVAB was collected from sika deer (*Cervus nippon*) in Taiwan fed with distiller's grains (a cereal byproduct of the distillation process). Velvet antlers were cut from the deer. The resulting velvet antlers were sliced, dried and ground into powders. DVAB was mixed with velvet antler at a ratio of 1:5 by weight to obtain the composition of the invention. MC3T3-E1 osteoblastic cells were seeded at a 96-well plate with a concentration of 2000 cells/well. The compositions of the invention at concentrations of 40 µg/ml, 20 µg/ml, 10 µg/ml and 5 µg/ml were added to the wells of the 96-well plate. After 24 hours, 90 µl of Minimum Essential Medium Alpha Modification medium (MEMα medium) and 10 µl of 3-(4,5-dimethylthiazol-2-yl)-2,5-diphenyltetrazolium bromide (MTT) were added to the wells of the 96-well plate for four hours. 50 µl of supernatants were taken from the wells and 200 µl of isopropone in 0.04N HCl solution were added thereto. The absorbance of the resulting solution was measured at 600 nm by ELISA Reader to calculate the cell survival rates. The combination indexes (CI) at $ED_{90}$, $ED_{75}$ and $ED_{50}$ of the composition of the invention (DVAB:velvet antler=5:1 (w/w)) are 0.49, 0.6 and 0.76, respectively. The combination indexes were calculated using CalcuSyn Version 2.0 that is the definitive analyzer of combined drug effects, able automatically to quantify phenomena such as synergism and inhibition (*Methods in Molecular Medicine, vol. 110: Chemosensitivity: Vol. 1: In Vitro Assays* Edited by: R. D. Blumenthal © Humana Press Inc., Totowa, N.J.). The combination index less than 1 indicates a synergistic effect.

Example 2

In vivo Assays for Evaluation of Efficacy of the Composition of the Invention in Treating and/or Preventing Osteoporosis DVAB was collected from sika deer (*Cervus nippon*) in Taiwan fed with distiller's grains (a cereal byproduct of the distillation process). Velvet antlers were cut from the deer. The resulting velvet antlers were sliced, dried and ground into powders. DVAB was mixed with velvet antler at a ratio of 1:5 by weight to obtain the composition of the invention (hereafter referred to as "DVAB composition"). In the example, sham group means that rats without ovariectomy (OVX) received 5 ml/kg ddH$_2$O; control group means that rats received 5 ml/kg ddH$_2$O; positive group means that DVAB Composition Decreases the Biomarker of Osteoporosis in Serum ALP In an ovariectomized rat model of osteoporosis, rats were divided into sham (5 ml/kg ddH$_2$O without ovariectomy) and ovariectomized (OVX) groups. The OVX rats were then subdivided into two groups orally treated with 5 ml/kg ddH$_2$O (control group) and DVAB composition (0.2 g/kg) daily for 20 weeks. The positive group refers to rats receiving 0.1 mg/5 ml/kg of ethinylestridiol. Body weight was monitored every 4 weeks and serum BGP (osteocalcin) was observed in the end point. The body weight of the DVAB composition group was significantly lower than the control group from 4$^{th}$ week to end, expressing the effectively estrogen-like effects against weight gain due to menopausal syndrome.

The ALP values in control group (OVX) were higher than the sham group. The ALP values of the DVAB composition group were significantly lower than the control group, expressing the effective anti-osteoporotic activity (see FIG. 1).

Biomechanical Strength Test

Figure 2:
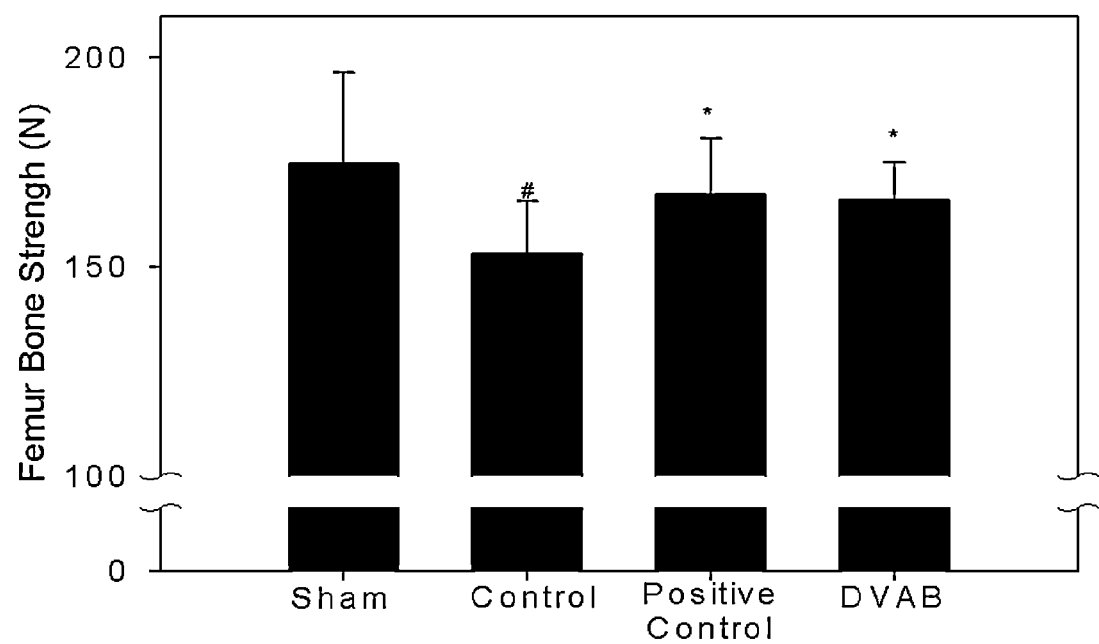
FIG. 2 shows the biomechanical strength of fumur in rats. #: $p<0.05$ vs sham group; *: $p<0.05$ vs control group.
Figure 3:
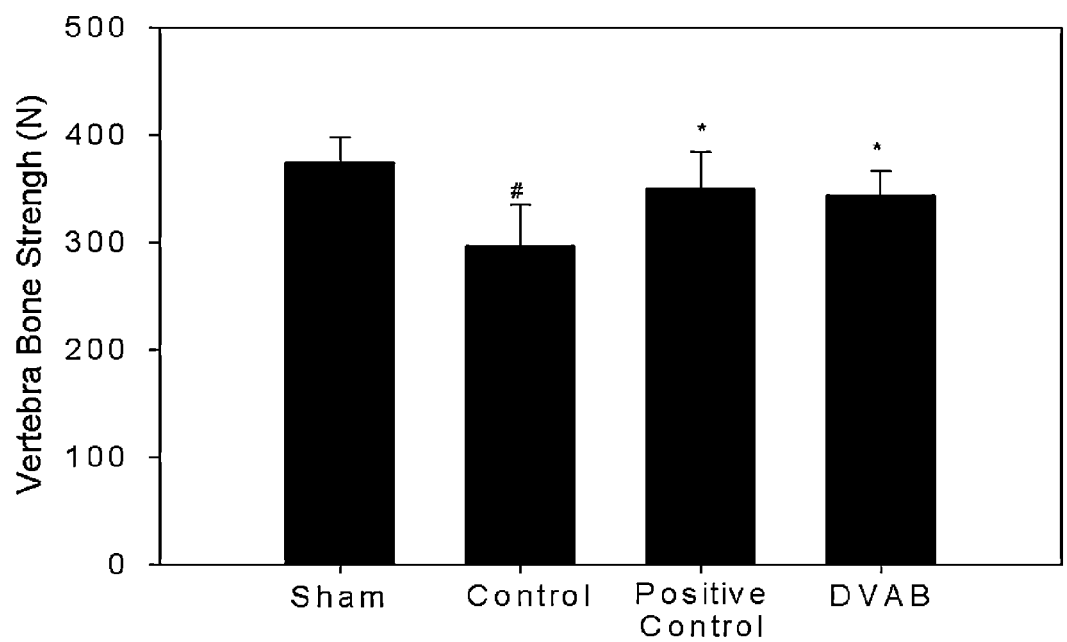
FIG. 3 shows the biomechanical strength of vertebra in rats. #: $p<0.05$ vs sham group; *: $p<0.05$ vs control group.

The strength of fumur and vertebra bones were assessed by three-point bending test and compression test, respectively (Xiao Xia Li et al., *Effects of Osthole on Postmenopausal Osteoporosis Using Ovariectomized Rats; Comparison to the Effects of Estradiol; Biol. Pharm.Bull.* 25(6) 738-742, 2002). The strength of fumur and vertebra bones in the control group were significantly weaker than the sham group. The both biomechanical strengths of femur and vertebra increased 9% (FIG. 2) and 16% (FIG. 3) respectively in DVAB composition treated OVX rats.

Bone Histomorphometry with Micro-CT

Figure 4:
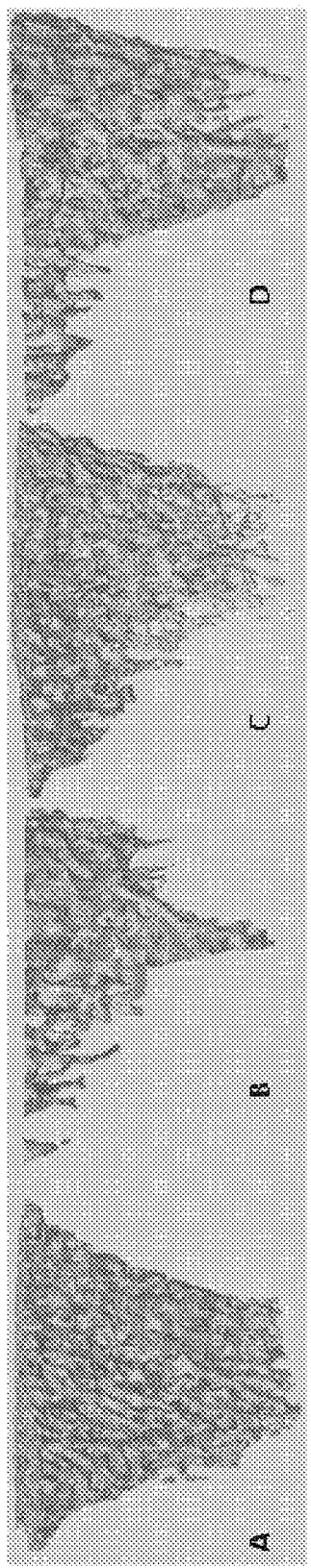
FIG. 4 shows bone histomorphometry photos of tibia trabecular bones of sham group (A), control group (B), positive control (C), DVAB composition group (D) from micro-CT.

Biomechanical strength also was measured by three-point bending test of femur and compression test of vertebra. Furthermore, the tibia from rats was measured by cancellous bone histomorphometry with micro-CT. In this study, percentage of bone volume (BV/TV), trabecular thickness (Tb, Th), trabecular number (Tb, N), trabecular separation (Tb, Sp) and structure model index (SMI) were measured. Assessments on the basis of biochemical, biomechanical, and histopathological parameters showed that DVBA composition has a definite anti-osteoporotic effect. Particularly, the trabecular bone mass of tibia in the control group were significantly lower than the sham group (FIG. 4 A and B), and bone mass was recovered with the DVAB composition (FIG. 5D). The results of cancellous bone histomorphometry by micro-CT showed the percentage of bone volume (BV/TV), trabecular number (Tb.N), trabecular separation (Tb.Sp), and structure model index (SMI) were reversed significantly in the DVAB composition group (see Table 1).

TABLE 1

The bone histomorphometry datameter of tibia trabecular bone from micro-CT.

| Groups | BV/TV (%) | Tb.Th (µm) | Tb.Sp (µm) | Tb.N (1/µm) | SMI |
| --- | --- | --- | --- | --- | --- |
| Sham | 40.84 +/− 10.73 | 101.66 +/− 16.09 | 168.28 +/− 29.25 | 0.0040 +/− 0.0004 | 0.60 +/− 0.38 |
| Control | 10.7. +/− 3.32# | 107.69 +/− 9.77 | 696.22 +/− 158.76# | 0.0010 +/− 0.0003# | 2.01 +/− 0.22# |
| Positive Control | 25.69 +/− 10.41* | 90.29 +/− 4.01 | 255.99 +/− 94.24* | 0.0028 +/− 0.0010* | 1.29 +/− 0.52# |
| DVAB | 16.15 +/− 2.23* | 105.60 +/− 2.63 | 447.25 +/− 65.28* | 0.0015 +/− 0.0001* | 1.70 +/− 0.10# | p < 0.05 vs sham group.
*p < 0.05 vs control group.

Example 3

Component Assay of DVAB Composition

DVAB composition of the invention and deer velvet antler alone were analyzed for estradiol, calcium and iron contained thereof. The results are shown in the able below.

| Component | DVAB composition of the invention | velvet antler |
| --- | --- | --- |
| Estradiol (ng/g) | 3.05 | 2.61 |
| Calcium (% w/w) | 13.2 | 13.3 |
| Iron (ppm) | 434 | 185 |

The above results show that amounts of estradiol and calcium in the DVAB composition of the invention and velvet antler do not have significant difference, indicating that estradiol and calcium did not affect the effect of anti-osteoporosis.

What is claimed is:

1. A composition for treating and/or preventing osteoporosis, comprising deer velvet antler blood (DVAB) in combination with velvet antler, wherein DVAB is in an amount of about 5% (w/w) to about 50% (w/w) and the velvet antler is in an amount of about 95% (w/w) to about 50% (w/w), and wherein the amount of iron in the composition ranging from about 200 ppm to about 500 ppm.

2. The composition of claim 1, wherein DVAB is in an amount ranging from about 10% (w/w) to about 35% (w/w).

3. The composition of claim 1, wherein DVAB is in an amount ranging from about 10% (w/w) to about 25% (w/w).

4. The composition of claim 1, wherein the velvet antler is in an amount ranging from about 90% (w/w) to about 60% (w/w).

5. The composition of claim 1, wherein the velvet antler is in an amount ranging from about 90% (w/w) to about 80% (w/w).

6. The composition of claim 1, which is in a dose from about 10 mg/kg body weight (BW) to about 300 mg/kg of BW per day.

7. The composition of claim 1, which can be administered systemically, topically or locally.

8. The composition of claim 1, which further comprises a pharmaceutically acceptable carrier.

9. The composition of claim 1, which can be administered orally.

10. The composition of claim 1, which is in the form of tablet, pill, capsule, liquid, gel, syrup, slurry or suspension.

11. The composition of claim 1, which can be used as a medicament or a food.

12. The composition of claim 1, which can be used as a dietary supplement.

13. The composition of claim 1, wherein the velvet antler is in a form of ethanol extract.

* * * * *